United States Patent [19]

Schulteis et al.

[11] 3,930,834
[45] Jan. 6, 1976

[54] ALGAECIDAL COMPOSITION
[75] Inventors: David T. Schulteis, Jackson; Donald E. Seymour, Shorewood, both of Wis.
[73] Assignee: Applied Biochemists, Inc., Mequon, Wis.
[22] Filed: Jan. 14, 1974
[21] Appl. No.: 433,239

[52] U.S. Cl. ................................ 71/67; 71/66
[51] Int. Cl.² ...................................... A01N 17/00
[58] Field of Search ................................ 71/66, 67

[56] References Cited
UNITED STATES PATENTS
| | | | |
|---|---|---|---|
| 2,734,028 | 2/1956 | Domogalla | 71/67 |
| 3,634,061 | 1/1972 | Geiger | 71/66 |
| 3,716,351 | 2/1973 | Kunkel et al. | 71/67 |

Primary Examiner—Lewis Gotts
Assistant Examiner—Catherine L. Mills
Attorney, Agent, or Firm—Andrus, Sceales, Starke & Sawall

[57] ABSTRACT

A method of preparing a copper complex for use in eliminating the growth of marine plant life such as algae. The copper complex is provided by initially reacting an insoluble copper compound with an aqueous solution of an acid to dissociate the copper ions, and thereafter chelating the released copper ions to form a copper complex. The resulting complex has improved stability to both heat and light and contains an increased amount of copper compared to copper complexes formed by prior methods, thereby making the complex more effective as an algaecide.

17 Claims, No Drawings

ALGAECIDAL COMPOSITION

BACKGROUND OF THE INVENTION

Rivers, lakes, streams, drinking water supplies, swimming pools, shower rooms, industrial water systems, and the like, are frequently polluted by the excessive growth of algae and other microorganisms which impart a distasteful appearance and odor to the water and generally interfere with the flow of the water and may be harmful to health.

Copper ions are known to be effective against the growth of algae. In the past water-soluble copper compounds, such as copper sulfate, have been used extensively as algaecides. Copper ions released by copper sulfate when added to water, react with carbonates or bicarbonates found in water to produce insoluble copper compounds which precipitate and cause turbidity or cloudiness in the treated water. If excessive amounts of insoluble copper compounds settle out, the compounds can form a sludge or deposit, which in the case of a lake or stream, may tend to destroy the fish life or zooplankton which is essential as fish food.

To overcome the problems associated with the use of copper sulfate, a complex formed by the reaction of copper sulfate and an alkanolamine, as disclosed in U.S. Pat. No. 2,734,028, has been used and has achieved wide success as an algaecide. A complex of this type has the ability to maintain the copper ions in solution, even when the algaecide is added to alkaline water containing high proportions of carbonates or bicarbonates, as well as soft water situations.

The copper alkanolamine complex of the type disclosed in U.S. Pat. No. 2,734,028 is normally packaged as a concentrated aqueous solution in glass, plastic or metal containers and is apt to be stored for extended periods. It has been found that when this complex is stored over long periods of time, and particularly when the containers may be subjected to sunlight and/or warm temperatures, decomposition of the complex occurs, resulting in a precipitation of copper. Precipitation of the copper removes the toxic copper ions from the solution and thus decreases the effectiveness of the complex when subsequently diluted and added to the water to be treated.

The copper complex prepared from copper sulfate has a further disadvantage in that the sulfate ions tend to combine with hydrogen in the aqueous solution to form sulfuric acid, which is highly corrosive, thereby presenting problems in handling, shipment and storage of the concentrated product.

The presence of the sulfate ions has a further disadvantage in that when the complex is added to the water to be treated in the recommended dosage, a sulfate content results of approximately 0.5 ppm per acre foot of water being treated. This high concentration of sulfates can be conducive to diatom blooms. Diatom requires sulphates for the uptake of silica for the cell walls. Furthermore, when copper sulphate is used as the starting material in forming the complex, the concentration of toxic copper ions is limited in the concentrated product, with a concentration of approximately 7% being the upper limit.

To avoid problems associated with the use of copper sulfate, attempts have been made in the past to utilize other copper-containing materials, such as copper carbonate as an algaecide, as disclosed in U.S. Pat. No. 3,634,061. Copper carbonate is relatively insoluble in water and large amounts of this material have to be used to obtain minimum algae control. Not only is this procedure costly, but the undissolved copper carbonate remains ineffectual as an algaecide in the aquatic environment and remains on the bottom of the body of water and can be toxic to fish and fish food organisms.

SUMMARY OF THE INVENTION

The invention relates to a novel method of preparing a copper complex for use as an algaecide. In accordance with the invention, the copper complex is produced by initially reacting a water-insoluble copper compound, such as copper hydroxide, copper carbonate, or copper oxide, with an acid in aqueous solution. In the case of copper carbonate, the reaction generates carbon dioxide and water, and after complete liberation of the carbon dioxide from the solution, a chelating agent, such as an alkanolamine, is added to chelate the released copper ions and form the copper complex.

The resulting complex has improved effectiveness as an algaecide due to the fact that the complex contains more than 9% elemental copper which is a substantial increase in elemental copper over a copper complex formed through the use of copper sulfate.

The complex formed by the method of the invention has improved stability to both heat and light with the result that copper will not precipitate from the solution over extended periods of exposure to high temperatures and/or sunlight. The improved stability provides a longer shelf life and greatly simplifies the storage and shipment requirements.

As the complex is formed without the use of sulfates, the concentrated solution contains no sulfate ions so that the concentrate is less corrosive than a complex formed through use of copper sulfate. The elimination of sulfates also eliminates the potential toxicity to fish and zooplankton which occurs in the presence of sulfates, and decreases the potential of a diatom bloom following application of the algaecide to water.

The method of the invention enables a lesser amount of the chelating agent to be utilized in forming the complex, and in the case of nitrogen-containing chelating agents, such as alkanolamines, reduces the overall nitrogen concentration of the treating solution and consequently decreases the polluting effect caused by the addition of the nitrogen-containing compound to the body of water.

DESCRIPTION OF THE PREFERRED EMBODIMENT

The copper complex of the invention is produced by initially reacting an insoluble copper compound with an aqueous acidic solution to dissociate the copper ions and thereafter chelating the released copper ions with a chelating agent.

The copper compound is water insoluble and may take the form of copper hydroxide, copper benzoate, cuprous oxide, cupric oxide, copper bicarbonate, copper carbonate, copper thiocyanate, and minerals, such as tenorite, paralmelaconite, cuptite, malachite, azurite, or chessylite, containing one or more of the above-named copper compounds as their components.

The acid to be used can be any conventional organic or inorganic acid. It is preferred, however, to use organic acids as certain inorganic acids may generate ions in the solution which are undesirable from either a toxicity or pollution standpoint. For example, nitric and phosphoric acid are not preferred, because they will contribute nitrogen and phosphate ions to the body of water being treated. Sulfuric acid is not preferred because it will add sulfate ions, and similarly, hydrochloric acid will add chlorine ions which can be toxic to fish and marine life. Thus, it is preferred to employ organic acids, such as citric, tartaric, oxalic, acetic, maleic, boric, gluconic, lauric, stearic, palmitic, adipic, caprinic, formic, gallic, lactic, malic, malonic, oleic, phthalic, salicylic, suberic, tannic, propionic, and the like. In general, the organic acid can contain from 1 to 22 carbon atoms. Amino acids, while they can be used, are not preferred in that they contribute nitrogen to the body of water being treated.

The finely divided or powdered copper compound is added to the aqueous solution of the acid and the amount of water in the acidic solution is not critical and can vary within wide limits. From a practical standpoint, the acidic solution preferably has a concentration of 10 to 30% acid on a volume to volume basis.

The acid is preferably used in a stoichiometric amount with respect to the copper compound so as to completely dissociate all the copper ions. An excess of the acid is not critical, although it will reduce the pH of the solution and tend to reduce the rate of chelation, for it has been found that the rate of chelation of the copper is increased as the pH of the solution is increased.

When copper carbonate is used and is added to the acidic solution, a reaction occurs which generates carbon dioxide and water. After all of the carbon dioxide has been evolved from the solution, as evidenced by the termination of effervescence, the chelating agent is added to the solution to chelate the copper ions. It is important to wait until all of the carbon dioxide has been discharged before adding the chelating agent to the solution, for it is believed that carbon dioxide will be absorbed by the chelating agent, thereby reducing the effectiveness.

The chelating agent is preferably an alkanolamine. The alkanolamine includes at least one or more alkanol groups containing 1 to 10 carbon atoms and may consist of one or more of the following compounds: aminoethylethanolamine, diethanolamine, triethanolamine, dimethylethanolamine, diethylethanolamine, monoethanolamine, monoisopropanolamine, diisopropanolamine, triisopropanolamine, methyldiethanolamine, or the like. Of the above named compounds, triethanolamine has been found to be a very effective material, because it requires a smaller amount of the triethanolamine, than the other amines to keep the copper ions in solution. In addition, the salts or esters of the above alkanolamines can be employed with equal results. To form the complex, the alkanolamine is generally used in a weight ratio of 1 : 2 parts per 1 part of the copper.

Other chelating agents which can be employed are tertiary amines such as methyldodecylbenzyl trimethyl tertiary amine, methyldodecylxylylene bis (trimethyl) tertiary amine, diisobutylphenoxyethoxy dimethyl benzyl tertiary amine, stearyl triemthyl tertiary amine, and the like; polyethylene glycols having an average molecular weight in the range of 200 to 4000; and water soluble organic acids containing 1 to 22 carbon atoms such as citric acid, gluconic acid, lactic acid, tartaric acid, ethylene diamine tetraacetic acid, and their water soluble salts.

The resulting complex will maintain the copper in solution in a variety of hard waters containing substantial concentrations of alkaline earth metal carbonates and bicarbonates, or in water containing high concentrations of dissolved carbon dioxide.

The solution containing the copper complex has a pH generally in the range of 8.0 to 10.0 and usually about 8.8. This pH is considerably higher than the pH of a solution containing the complex formed through use of copper sulfate, which is generally about 7.56. This increased pH is believed to contribute to the increased amount of elemental copper in the complex, for the rate of chelation is increased with an increase in pH. Thus, the solution containing the copper complex as prepared by the invention contains 9% by weight or more of elemental copper, as compared with an elemental copper concentration of about 7% in the solution containing the complex prepared from copper sulfate. This substantial increase in the amount of elemental copper produces a marked increase in effectiveness of the solution as an algaecide.

The complex prepared by the method of the invention has improved heat and light stability over the complex prepared from copper sulfate and the copper will not precipitate from solution over extended periods when exposed to either extreme temperatures or sunlight. The increase in stability is completely unexpected in that one would expect the copper complex, whether it be derived from copper sulfate or copper carbonate, to have approximately the same stability to various environmental parameters, such as light and temperature. However, the copper complex derived through the invention demonstrates a substantial increase in stability as compared to the copper complex derived from copper sulfate. It is believed that this increase in stability is achieved because of the elimination of the sulfate ions in solution, for the sulfate ions can form sulfuric acid in solution which act on the chelated complex to release copper over extended periods of time.

Because the copper is retained in solution, the entire toxic effect of the copper as an algaecide is realized thereby achieving a saving in the amount of copper and in total algaecide used, with a resulting saving in total cost per acre treated.

As a further advantage, a lesser amount of the alkanolamine is required per unit volume in preparing the complex and this reduces the overall nitrogen content of the solution and reduces unwanted nutrients which are contributed by the nitrogen.

The solution containing the copper complex is normally stored, handled and transported as a concentrate containing about 8 to 35% by weight of elemental copper and generally about 9.5% and containing about 50 to 80% by weight of the complex. The concentrated solution normally is diluted at the time of use in a ratio of 5 to 20 parts of water for each part of the concentrated solution. The diluted solution is applied to the body of water such that the body of water contains from about 0.25 to 20.0 ppm by weight of elemental copper.

Instead of using the copper complex in the form of an aqueous solution, the complex can be adsorbed on an inert particulate carrier and the dry carrier can then be applied to the water surface. In this case, the concentrated solution of the complex is sprayed onto the carrier particles to coat and impregnate the particles with the complex. The particles are then air dried, preferably in a rotating drum or tumbler to evaporate the water. The resulting particles, while containing some moisture, are free-flowing and essentially dry to the touch. In the dry state, the impregnated carrier particles contain from about 1 to 50% by weight of the complex and 99 to 50 % by weight of the inert material.

When applied to the water surface, the particles impregnated with the copper complex will sink to the bottom, and as such, the impregnated particles are particularly useful in treating bottom-attached algae, such as Chara, Nitella and Tolypella, and in treating bottom growths of filamentous algae. To achieve this function, the particle size of the particles is important, and should be in the range of 8 to 16 mesh. If the particle size is smaller than this range, the particles may tend to float and not sink to the bottom and have a greater tendency to be windblown during application. On the other hand, if the particle size is larger than the above-mentioned range, the surface area per unit volume of the particles is reduced, with the result that a lesser quantity of the copper-complex can be adsorbed on the particles, thereby requiring additional quantities of the impregnated particles to achieve algaecidal control.

In addition, the carrier particles should have a bulk density in the range of 0.5 to 15gr/cc in order to obtain the desired absorption of the copper complex.

It has been found that Attapulgite clay (soft, RVM type) and Celaton clay are particularly satisfactory for use as the carrier. These clays have bulk densities in the aforementioned range and tend to break down to a fine powder when immersed in water. A mixture of about 50 to 95 % by weight of Attapulgite clay and 5 to 50 % by weight of Celaton clay is preferred.

The algaecideal composition is effective against all common forms of algae, including filamentous algae such as Cladaphora and Spirogya, planktonic algae such as Anacystis and Anaebena, chara algae such as *Chara vulgaris* and Nitella and swimming pool algae such as black, brown and red algae.

In addition, the copper complex formed by the method of the invention has been found to be effective as a herbicide against certain vascular aquatic plants, such as *Hydrilla verticillata* and *Potamogeton crispus* (curly leaf pond weed).

The following examples illustrate the preparation of the copper complex of the invention.

EXAMPLE I 5 gallons of copper triethanolamine complex were prepared by mixing 5625 ml of water with 1875 ml of 98% by weight glacial acetic acid. To this mixture, 2270 grams of powdered copper carbonate were added and the reaction was allowed to proceed to completion as evidenced by the termination of the discharge of carbon dioxide. 500 ml of triethanolamine was then added to the solution to chelate the copper ions and the resulting aqueous solution contained 9.5% by weight of elemental copper.

EXAMPLE II 25 grams of oxalic acid was dissolved in 75 ml of water. 50 grams of copper carbonate was slowly added and the reaction was allowed to go to completion. This was evidenced by the termination of effervescing of carbon dioxide from the reaction media. Finally 100 grams of monoethanolamine was added for the purpose of chelating the dissociated cupric ions. The resulting solution had a clear, dark blue color and contained approximately 10 % by weight of elemental copper.

EXAMPLE III 20 ml of concentrated nitric acid was added to 80 ml of water. 50 grams of copper carbonate was slowly added and the reaction was allowed to go to completion, as evidenced by the termination of effervescing of carbon dioxide from the reaction media. Finally, 100 grams of Quadrol [N,N,N',N',-tetrakis(2-hydroxy-propyl) ethylenediamine] was added for the purpose of chelating the dissociated cupric ions. The resulting color of the solution was a clear, dark blue color indicating a high concentration of elemental copper of approximately 9.5%

EXAMPLE IV 25 grams of citric acid anhydrous was added to 75 ml of water. 62.5 grams of cupric hydroxide was added and the reaction was allowed to go to completion. 50 ml of triethanolamine and 50 ml of tridecyldimethyl benzyl tertiary amine were then added for the purpose of chelating the cupric ions. The resulting color of the solution was a clear, dark blue color indicating a stable copper complex. This complex was approximately 20% elemental copper.

LIGHT STABILITY TEST

A series of samples of the concentrated solution prepared in accordance with Example I were stored in glass containers and subjected to ultra violet light. After a period of three months there was no visible deposit or precipitation in the containers, as well as no significant measurable loss of copper from solution as measured by instrumentation designed for copper assay measurements.

A second series of samples were prepared using copper sulfate to produce the complex as disclosed in U.S. Pat. No. 2,734,028. In preparing these samples, 100 ml of triethanolamine was added to 90 ml of water and enough copper sulfate was dissolved in the solution to produce a 7.1% by weight solution of elemental copper. Samples of the concentrated solution containing the complex produced through use of copper sulfate were stored in glass containers and subjected to ultra violet light. After a period of 91 days, over one-half percent of the copper had precipitated out on the sides and bottom of the vessel.

This test indicates the substantial improvement in stability to light of the complex produced by the method of the invention, as compared to that produced from copper sulfate.

HEAT STABILITY TEST

A series of samples of the concentrated solution prepared in Example I were stored in an incubation oven at a temperature of 104°F. After a period of three months there was no visible deposit or precipitation of copper in the containers and there was no measurable loss of copper from the solutions as determined by instrumentation.

Similar samples of the concentrated solution of the complex produced from copper sulfate, prepared by the method outlined above, were similarly subjected to a temperature of 104°F in an incubation oven. After a period of 91 days, the solution prepared from copper sulfate had lost over one half percent of the copper as a precipitate on the sides and bottom of the vessel.

The heat stability test shows the substantial improvement in heat stability achieved by the complex prepared by the method of the invention, as compared to that prepared from copper sulfate.

WATER HARDNESS STABILITY

The concentrated solutions prepared in accordance with Example I were diluted with water to one gallon samples containing 0.4 ppm of elemental copper. The water of dilution used in one group of samples had a hardness of 30 ppm as carbonate hardness, the water of dilution used in a second group of samples had a harndess of 100 ppm and the water used in a third group of samples had a hardness of 300 ppm. Over a period of 7 days, no copper was observed as precipitating out of the diluted solutions.

ALGAECIDAL EFFECTIVENESS TESTS

Cultures of Cladophora, a green filamentous algae, were grown in one gallon glass containers in the laboratory, under a 16 hour photoperiod and a temperature of 75°F. Cladophora is one of the most common nuisance algae which occurs in lakes and ponds. To the vigorously growing algae, evidenced by heavy green growth, the copper complex prepared according to Example I was added to obtain a copper concentration of 0.2 ppm in the gallon container. Within 48 hours, the Cladophora turned white and sank to the bottom of the container. Microscopic examination of this algae showed that the algae cells were chlorotic and either in the dead or dying condition. Examination of the surrounding solution resulted in a copper content of 0.06 ppm, as compared to 0.2 ppm originally, which suggests that the missing copper was taken up or absorbed by the algae, resulting in the death of the algae. Control samples of algae to which only distilled water was added after the 48 hours were still exhibiting vigorous growth.

EXAMPLE B

Cultures of Aphanizomenon flos-aqua, a green planktonic algae, were grown under conditions described in Example A. The copper complex prepared as described in Example I was added to the cultures to obtain a copper concentration of 0.2 ppm. After 24 hours the cultures to which the copper complex was added were practically clear of planktonic algae. The algae had turned white and had sunk to the bottom of the containers.

EXAMPLE C

A body of water one-half acre in size with an average depth of 8 feet and having a heavy infestation of Chara, a bottom attached algae, was treated with the copper complex prepared as described in Example I and adsorbed onto an inert clay carrier composed of, 41% by weight of Attapulguite clay and 16% by weight of Celaton clay. The resulting dry granular preparation contained 96% by weight of the inert carrier and 4% by weight of the copper complex and was applied at a rate of 60 pounds per surface acre, resulting in a copper concentration in the bottom two feet of water of 0.4 ppm of copper. Three days after application, the Chara was under complete control. It had turned white and was breaking apart. No fish deaths were observed and no noticeable harm was done to the aquatic environment or ecosystem.

EXAMPLE D

The copper complex as prepared in Example I was added to a swimming pool to obtain a copper concentration of 0.2 ppm. No staining of the pool walls resulted from the addition of the algaecide to the pool water and even super chlorination following the addition of the algaecide did not result in staining. Algae which were present in the pool were controlled, as well as any reinfestation of new algae. The algae which was present in the pool was Oscillatoria.

Various modes of carrying out the invention are contemplated as being within the scope of the following claims particularly pointing out and distinctly claiming the subject matter which is regarded as the invention.

I claim:

1. An algaecide composition having improved stability, comprising an aqueous solution containing an algaecidal effective amount of a copper complex produced by reacting a water-insoluble copper compound selected from the group consisting of (a) copper carbonate, (b) copper oxide, (c) copper hydroxide, (d) copper bicarbonate, (e) copper benzoate, (f) copper thiocyanate and (g) naturally occurring copper minerals containing at least one of said (a)–(f) inclusive with an aqueous solution of an acid in sufficient amount to dissociate the copper ions from said compound, said acid selected from the group consisting of an inorganic acid and an organic acid having from 1 to 22 carbon atoms in the molecule, and thereafter chelating the copper ions with a chelating agent selected from the group consisting of (a) an alkanolamine having at least one alkanol group containing from 1 to 10 carbon atoms in the molecule, (b) polyethylene glycols having an average molecular weight in the range of 200 to 4000, (c) tertiary amines and (d) carboxylic acids having 1 to 22 carbon atoms in the molecule and (e) water soluble salts of (d), to provide the complex.

2. The composition of claim 1, wherein said aqueous solution contains at least 9% by weight of elemental copper.

3. The composition of claim 1, wherein the copper compound is copper carbonate, and the chelating agent is triethanolamine.

4. The composition of claim 1, wherein the alkanolamine is used in a weight ratio of 1 to 2 parts per 1 part of copper.

5. An algaecide composition, comprising a plurality of generally inert particles and a copper complex absorbed on said particles, said complex produced by reacting a water-insoluble copper compound selected from the group consisting of (a) copper carbonate, (b) copper oxide (c) copper hydroxide, (d) copper bicarbonate (e) copper benzoate, (f) copper thiocyanate and (g) naturally occuring copper minerals containing at least one of said (a)–(f) inclusive with an aqueous solution of an acid in sufficient amount to dissociate the copper ions from said compound, said acid selected from the group consisting of an inorganic acid and an organic acid having from 1 to 22 carbon atoms in the molecule, and thereafter chelating the copper ions with a chelating agent selected from the group consisting of (a) an alkanolamine having at least one alkanol group containing from 1 to 10 carbon atoms in the molecule, (b) polyethylene glycols having an average molecular weight in the range of 200 to 4000, (c) tertiary amines and (d) carboxylic acids having 1 to 22 carbon atoms in the molecule and (e) water soluble salts of (d), to provide the complex.

6. The composition of claim 5, wherein the particles, have a size in the range of 8 to 16 mesh.

7. The composition of claim 6 wherein the particles have a bulk density in the range of 0.5 to 15 gr./cc.

8. The composition of claim 6 wherein the particles are clay and are characterized by the ability to break up into a fine powder when exposed to water.

9. The composition of claim 8 wherein the particles are selected from the group consisting of Atapulgite clay and Celaton clay.

10. The method of preparing an algaecide composition having improved stability, comprising the steps of reacting a water insoluble copper compound selected from the group consisting of (a) copper carbonate (b) copper oxide, (c) copper hydroxide, (d) copper bicarbonate, (e) copper benzoate, (f) copper thiocyanate and (g) naturally occurring copper minerals containing at least one of said (a)-(f) inclusive with an aqueous solution of an acid in sufficient amount to dissociate the copper ions from said compound, said acid selected from the group consisting of an inorganic acid and an organic acid having from 1 to 22 carbon atoms in the molecule, and thereafter chelating the copper ions with a chelating agent selected from the group consisting of (a) an alkanolamine having at least one alkanol group containing from 1 to 10 carbon atoms in the molecule, (b) polyethylene glycols having an average molecular weight in the range of 200 to 4000, (c) tertiary amines and (d) carboxylic acids having 1 to 22 carbon atoms in the molecule and (e) water soluble salts of (d), to provide the complex.

11. The method of claim 10, wherein the solution contains more than 9% by weight of elemental copper in the form of the copper complex.

12. The method of claim 10, wherein the chelating agent is alkanolamine and is used in a weight ratio of 1 to 2 parts per 1 part of copper.

13. The method of claim 10, wherein said copper compound is copper carbonate, said first named acid is acetic acid and said chelating agent is triethanolamine.

14. The method of claim 10 wherein the acid is substantially free of nitrogen, sulfur, phosphorus and halogens.

15. A method of controlling the growth of algae in a body of water, comprising the step of bringing into contact with the algae an aqueous solution of a copper complex produced by reacting a water-soluble copper compound selected from the group consisting of (a) copper carbonate, (b) copper oxide, (c) copper hydroxide, (d) copper bicarbonate, (e) copper benzoate, (f) copper thiocyanate and (g) naturally occurring copper minerals containing at least one of said (a)-(f) inclusive with an aqueous solution of an acid in sufficient amount to dissociate the copper ions from said compound, said acid selected from the group consisting of an inorganic acid and an organic acid having from 1 to 22 carbon atoms in the molecule, and thereafter chelating the copper ions with a chelating agent selected from the group consisting of (a) an alkanolamine having at least one alkanol group containing from 1 to 10 carbon atoms in the molecular, (b) polyethylene glycols having an average molecular weight in the range of 200 to 4000, (c) tertiary amines and (d) carboxylic acids having 1 to 22 carbon atoms in the molecule and (e) water soluble salts of (d), to provide the complex.

16. The method of claim 6, wherein the solution is added to the body of water in an amount such that the body of water contains from 0.25 to 20 ppm of the complex.

17. The method of claim 15, wherein the first named acid is substantially free of nitrogen, sulfur, phosphorus and halogens.

* * * * *

UNITED STATES PATENT AND TRADEMARK OFFICE
CERTIFICATE OF CORRECTION

PATENT NO. : 3,930,834
DATED : January 6, 1976
INVENTOR(S) : DAVID T. SCHULTEIS ET AL It is certified that error appears in the above–identified patent and that said Letters Patent are hereby corrected as shown below:

Column 8, Line 33 (CLAIM 1) Cancel "(a)" and substitute therefor ---(a')---, Column 8, line 35, Cancel "(b)" and substitute therefor ---(b')---, Column 8, line 37, Cancel "(c)" and substitute therefor ---(c')---, Column 8, Line 38, Cancel "(e)" and substitute therefor ---(e')---, Column 8, Line 39, Cancel "(d)" and substitute therefor ---(d')---, Column 8, Line 50 (CLAIM 5), Cancel "ab" and substitute therefor ---ad--- Column 8, Line 64, Cancel "(a)" and substitute therefor ---(a')--- Column 8, Line 66, Cancel "(b)" and substitute therefor ---(b')--- Column 8, Line 67, Cancel "(c)" and substitute therefor ---(c')--- Column 8, line 68, Cancel "(d)" and substitute therefor ---(d')---, Column 9, line 1, Cancel "(e)" and substitute therefor ---(e')---, Cancel "(d)" and substitute therefor ---(d')---, Column 9, line 3, (CLAIM 6), After "particles" delete "," (the comma), Column 9, line 29 (CLAIM 10), Cancel "(a)" and substitute therefor ---(a')---, Column 9, line 31 Cancel "(b)" and substitute therefor ---(b')---, Column 9, line 32, Cancel "(c)" and substitute therefor ---(c')---, Column 9, line 33 Cancel "(d)" and substitute therefor ---(d')---, Column 9, line 34, Cancel "(e)" and substitute therefor ---(e')---, Column 9, line 34, Cancel "(d)" and substitute therefor ---(d')---, Column 10, line 24, (CLAIM 15) Cancel "(a)" and substitute therefor ---(a')---, Column 10, line 26, Cancel "(b)" and substitute therefor ---(b')---, Column 10, Line 28, Cancel "(c)" and substitute therefor ---(c')---, Column 10, line 28, Cancel "(d)" and substitute therefor ---(d')---, Column 10, line 30 , Cancel "(e)" and substitute therefor ---(e')---, Cancel "(d)" and substitute therefor ---(d')---. Column 8, line 37 (CLAIM 1) Cancel "(d)" and substitute therefor ---(d')---:

Signed and Sealed this twenty-seventh Day of April 1976

[SEAL]

Attest:

RUTH C. MASON
Attesting Officer

C. MARSHALL DANN
Commissioner of Patents and Trademarks